(12) United States Patent
Condreva

(10) Patent No.: US 6,295,873 B1
(45) Date of Patent: Oct. 2, 2001

(54) ULTRASONIC SENSOR AND METHOD OF USE

(75) Inventor: Kenneth J. Condreva, Livermore, CA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 09/358,549

(22) Filed: Jul. 22, 1999

(51) Int. Cl.[7] ............ G01N 29/18; G01N 29/02
(52) U.S. Cl. ............ 73/597; 73/64.53; 73/61.79
(58) Field of Search .................. 73/64.53, 61.79, 73/597, 290 V, 61.41, 61.45, 61.43

(56) References Cited

U.S. PATENT DOCUMENTS

| | | | |
|---|---|---|---|
| 3,553,636 | * | 1/1971 | Baird ................... 73/64.53 |
| 3,985,030 | * | 10/1976 | Charlton ................ 73/290 V |
| 4,145,917 | * | 3/1979 | Brazhnikov et al. ........ 73/64.53 |
| 4,630,482 | | 12/1986 | Traina .................... 73/597 |
| 5,060,507 | | 10/1991 | Urmson et al. ........... 73/24.01 |
| 5,255,564 | * | 10/1993 | Glad et al. .............. 73/64.53 |
| 5,333,162 | | 7/1994 | Condreva ................. 377/20 |
| 5,473,934 | | 12/1995 | Cobb .................... 73/61.49 |

* cited by examiner

Primary Examiner—Hezron Williams
Assistant Examiner—Nashmiya Fayyaz
(74) Attorney, Agent, or Firm—Dickson G. Kehl; James C. Durkis; Virginia B. Caress

(57) ABSTRACT

An ultrasonic sensor system and method of use for measuring transit time though a liquid sample, using one ultrasonic transducer coupled to a precision time interval counter. The timing circuit captures changes in transit time, representing small changes in the velocity of sound transmitted, over necessarily small time intervals (nanoseconds) and uses the transit time changes to identify the presence of non-conforming constituents in the sample.

9 Claims, 4 Drawing Sheets

ULTRASONIC SENSOR AND METHOD OF USE

GOVERNMENT RIGHTS

The United States Government has rights in this invention pursuant to Contract No DE-ACO4-94AL85000 between the U.S. Department of Energy (DOE) and Sandia Corporation.

FIELD OF THE INVENTION

The present invention relates to an apparatus and method to measure the transit time of an ultrasonic wave through a sample, specifically useful for identifying characteristics of interest in liquid samples.

BACKGROUND OF THE INVENTION

Certain characteristics of liquids have traditionally been measured in order to develop a composite of the overall quality of the liquid. Liquid characteristics that have been measured to develop such a composite include the following: pH, turbidity, amount of dissolved oxygen, suspended solids, and dissolved solids. Devices used for performing these measurements (specific examples being the pH meter and dissolved oxygen and turbidity probes) typically require special handling, frequent adjustment, and manual calibration.

Sensor probes for remotely monitoring impurity levels in a liquid, such as water, are typically based on pH sensors, which require special handling and periodic calibration, thus limiting their use in remote applications. Other sensors for water, such as dissolved oxygen and turbidity probes, require even more frequent calibration. Water sampling kits, such as the Hach Kit, are inexpensive; however, the need for manual intervention during tests using such equipment is high, therefore rendering the process costly and inconvenient. Also, known sensors for monitoring liquids in process control systems in manufacturing must be vigilantly maintained, adjusted, and manually calibrated by specially trained technicians. Because of the harsh environments within which some of the known sensors must be capable of operation, they are expensive to maintain, as well as to buy.

U.S. Pat. No. 5,473,934, "Ultrasonic Fluid Composition Monitor," issued to Wesley Cobb on Dec. 12, 1995, describes a method of, and apparatus for, continuously monitoring the composition of a fluid mixture traveling through a conduit, where the fluid mixture can be a liquid/liquid or a liquid/solid. Ultrasonic propagation parameters and temperature are measured and compared to calibrated data based on analytical measurements of samples of the process fluid mixtures. Since this monitor is directed only to analyzing a flowing sample with equipment clamped to the outside of a conduit; it is not conducive to field (remote) use.

U.S. Pat. No. 5,060,507, "Method and Apparatus for Fluid Mixture Monitoring, Constituent Analysis, and Composition Control," issued to John Urmson, et al, on Jun. 21, 1989, describes another method and apparatus for fluid mixture monitoring and controlling using an acoustic sensing technique. A fluid sample and a reference fluid in elongated chambers are pulsed by sound waves; the system senses either the resonant frequencies in the chambers or the time lapse for the sound waves to traverse the chambers and determines composition of the fluid mixture by ratiometrically comparing the time-based measurements. The complexity of the device and the nature of the interaction between the reference fluids indicate that this monitor is also not conducive to field work.

U.S. Pat. No. 4,630,482, "Method and Apparatus for Ultrasonic Measurements of a Medium," issued to John Traina on Jun. 17, 1985, describes yet another method and apparatus for measuring the time required for an ultrasonic tone burst to traverse a medium from a transmitter to a receiver. Two transducers are required; a demodulator for high turbulence environments is preferred.

There is a need for a simple sensor system designed to speedily and easily identify chosen characteristics in liquids that avoids the problems typical of known monitors, i.e., complex equipment, elaborate electronics, complex sampling techniques, continual maintenance, frequent adjustment, and manual adjustment. There is also a need for a low-maintenance sensor system suitable for remote operation, i.e., that can be used without human operators and/or in situ. There is, still further, an ongoing need for miniaturized, easily handled sensor systems.

SUMMARY OF THE INVENTION

Accordingly, the above-identified needs are met by the present invention, which provides a sensor system that measures transit time through a sample to detect non-uniform or non-conforming constituents in a liquid sample. Differences in transit time through the actual sample, in comparison to a predetermined reference transit time through a "pure" sample, represent small changes in the velocity of sound transmitted.

The sensor system of the invention is capable of remote operation. "Remote," as used herein, is defined as the capability of autonomous and/or in situ function, i.e., the present invention may be operated away from a testing facility and human operators, and does not need to be "plugged in" or connected to other equipment.

The inventive system comprises at least one ultrasonic transducer coupled to a precision electronic timing circuit to detect transit time and a means for comparing reference transit time data obtained in a calibration step to data obtained during testing, all in a package suitable for autonomous operation. The timing circuit captures changes in transit time over the necessarily small time intervals (nanoseconds) required. The entire system may be miniaturized. For example, it is anticipated that miniature piezoelectric ultrasonic transducers may be used to stimulate responses.

In operation, using a liquid sample as an example, a pulse of ultrasonic energy is applied to the sample in a vessel of known dimensions. The elapsed time between the applied pulse and an echo signal from the opposite end of the vessel (i.e., transit time) is precisely measured. The properties of the pure liquid and the reference transit time have been predetermined in the only calibration step required for this system and have been programmed into the apparatus. Data representing transit time through the actual sample are obtained and compared to the predetermined transit time. Differences (even very small changes) between the actual transit time and the reference transit time indicate changes in the liquid's physical characteristics, more specifically in the purity of the liquid, and those changes are communicated to the user.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWING(S)

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

The present invention provides a small, rugged, low-cost, low-maintenance sensor, which includes at least one ultrasonic transducer and a low-power electronic timing circuit for making precise transit time measurements. In the preferred embodiment, the transducer(s) are miniature and the timing circuit is more specifically a precision timing interval counter (TIC). The sensor system of the invention measures variation in transit time of an ultrasonic wave, in comparison to a pre-determined reference transit time, through a liquid sample; the variations in transit time are representative of changes in certain properties of the sample. Using the variation in actual transit time from the reference transit time, the inventive sensor system is then used to identify non-conforming constituents in a liquid. This invention exploits the fact that the velocity of sound through a liquid varies with the concentration of impurities present in the liquid, and transit time is a function of sonic velocity. For example, the transit time of seawater varies by about one percent for a one-percent change in salinity.

Figure 1:
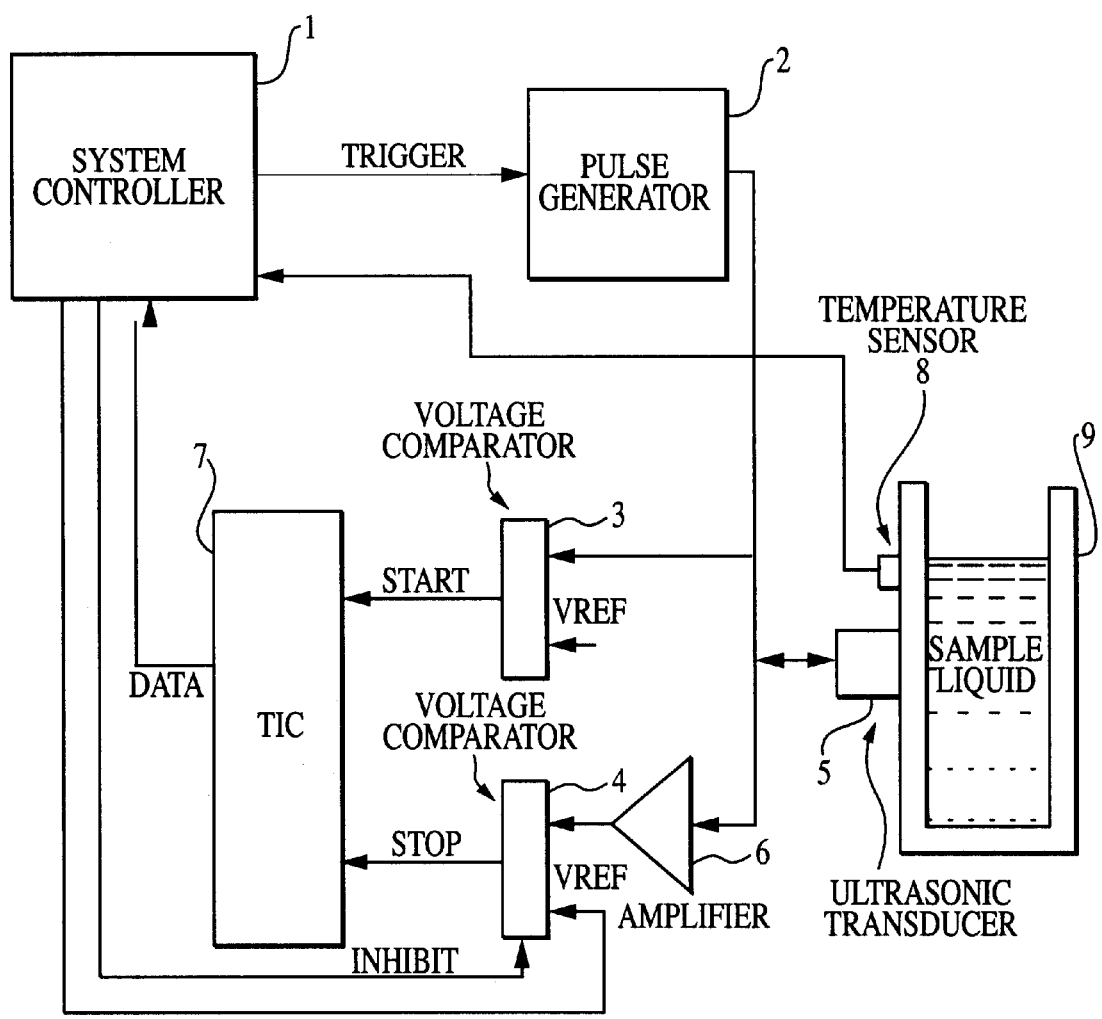
FIG. 1 is a block diagram showing the major components of a preferred embodiment of the invention in a single transducer system.

FIG. 1 is a block diagram showing the major component parts of a preferred embodiment of the present invention. The invention, according to FIG. 1, comprises a system controller 1 connected to a pulse generator 2 and two voltage comparator circuits 3 and 4. As shown in FIG. 1, the liquid sample is contained in a vessel 9; pulse generator 2 is connected in operable communication with one wall of vessel 9. The pulse generator 2 output (a stimulus signal) is connected to an ultrasonic transducer 5, voltage comparator 3, and an echo signal amplifier 6; the stimulus signal from pulse generator 2 acts as a drive signal for ultrasonic transducer 5 and voltage comparator 3. The amplifier 6 output is also connected to voltage comparator 4. Amplifier 6 is used to amplify the ultrasonic wave returned by transducer 5 after it has passed through the sample, i.e., the echo signal. An amplifier is not required for the sensor system if it is determined that the echo signal is strong enough to effect an output signal from voltage comparator 4. Both the reference voltage and the inhibit signal for voltage comparator 4 are provided by system controller 1. The output signals from voltage comparator 3 and 4 are connected to the start and stop inputs of a TIC circuit 7. The TIC 7 digital outputs are connected to system controller 1. System controller 1 also connects to the output of a temperature sensor 8 affixed to a vessel 9, which contains the sample to be tested. Although measuring the temperature of the sample greatly increases the accuracy of the measurements, in the event that the temperature of the sample is otherwise controlled, temperature sensor 8 would not be necessary.

System controller 1 computes the sample property of interest by comparison of obtained data to calibration data that has been programmed into system controller 1. System controller 1 is "pre-calibrated" with known values for the specific sample to be tested. Calibration in connection with the present invention is defined to mean the determination of the response or reading of an instrument relative to a series of known values over the range of the instrument. In manufacturing the inventive sensor for use, it is calibrated once using data obtained from a reference sample, then made (constructed) to a tolerance chosen for the specific "real-time" sample being tested. Once the calibration is performed, the sensor system of this invention can be used to measure the desired property of interest in the liquid sample.

Figure 2:
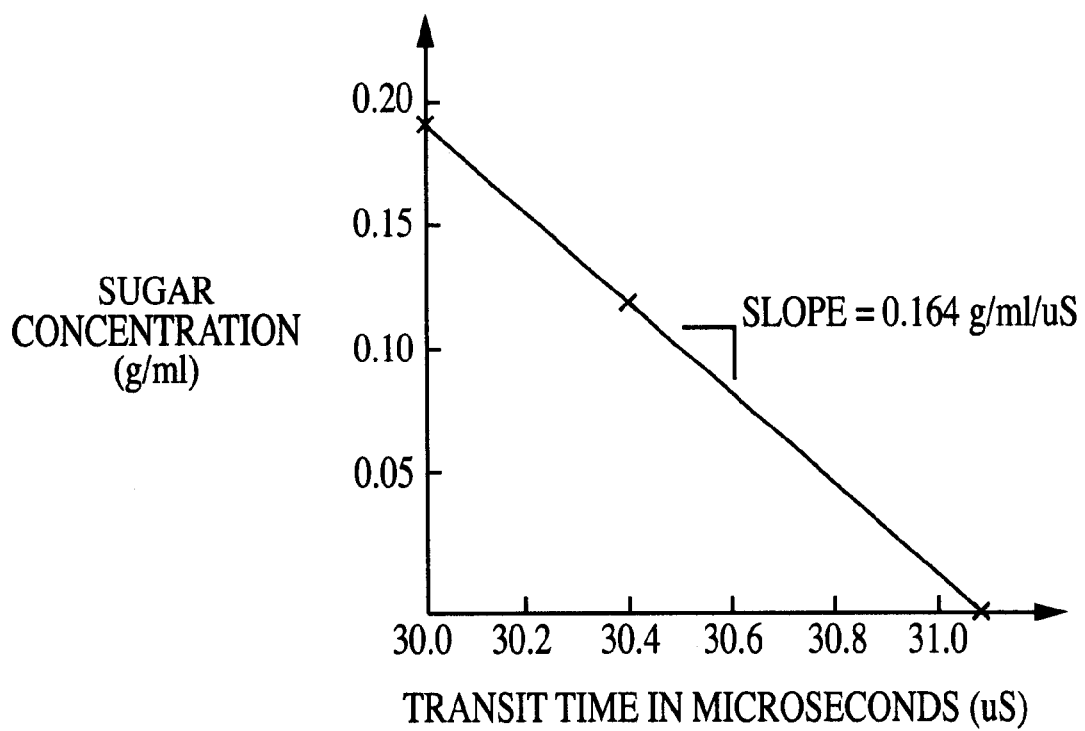
FIG. 2 is a graph of transit time measurements versus sugar concentration in water.

FIG. 2 is an example of the only calibration step needed for the present invention. The graph in FIG. 2 shows how calibration data is obtained simply and speedily in advance from a reference sample by plotting measurement of transit times in microseconds (horizontal axis) versus concentration of aqueous sugar solutions (using sugar in deionized water) in g/ml (vertical axis). Data was taken for various solutions by an apparatus similar to that of FIG. 1 in a vessel of dimension 0.9 inches, at a constant temperature of 18° Centigrade. The characteristic of interest, e.g., sugar concentration, was calculated from measured TIC 7 elapsed time data, i.e., transit time. In this example, sugar concentration (Cs), was obtained from the transit time measurement (Tt) by applying the linear relationship $Cc=(0.164 \text{ g/m/uS}) *(31.1-Tt)$, where Cc is sugar concentration in grams/milliliter, and Tt is transit time in microseconds. In this example, concentration is only a function of transit time. If a family of curves is obtained at different temperatures, then the temperature value is also included in the computation of Cc. The graph in FIG. 2 can be generated using any liquid of interest with any known additive or any known property change of interest. In the field, concentration versus transit time can be obtained for any fixed vessel.

Figure 3:
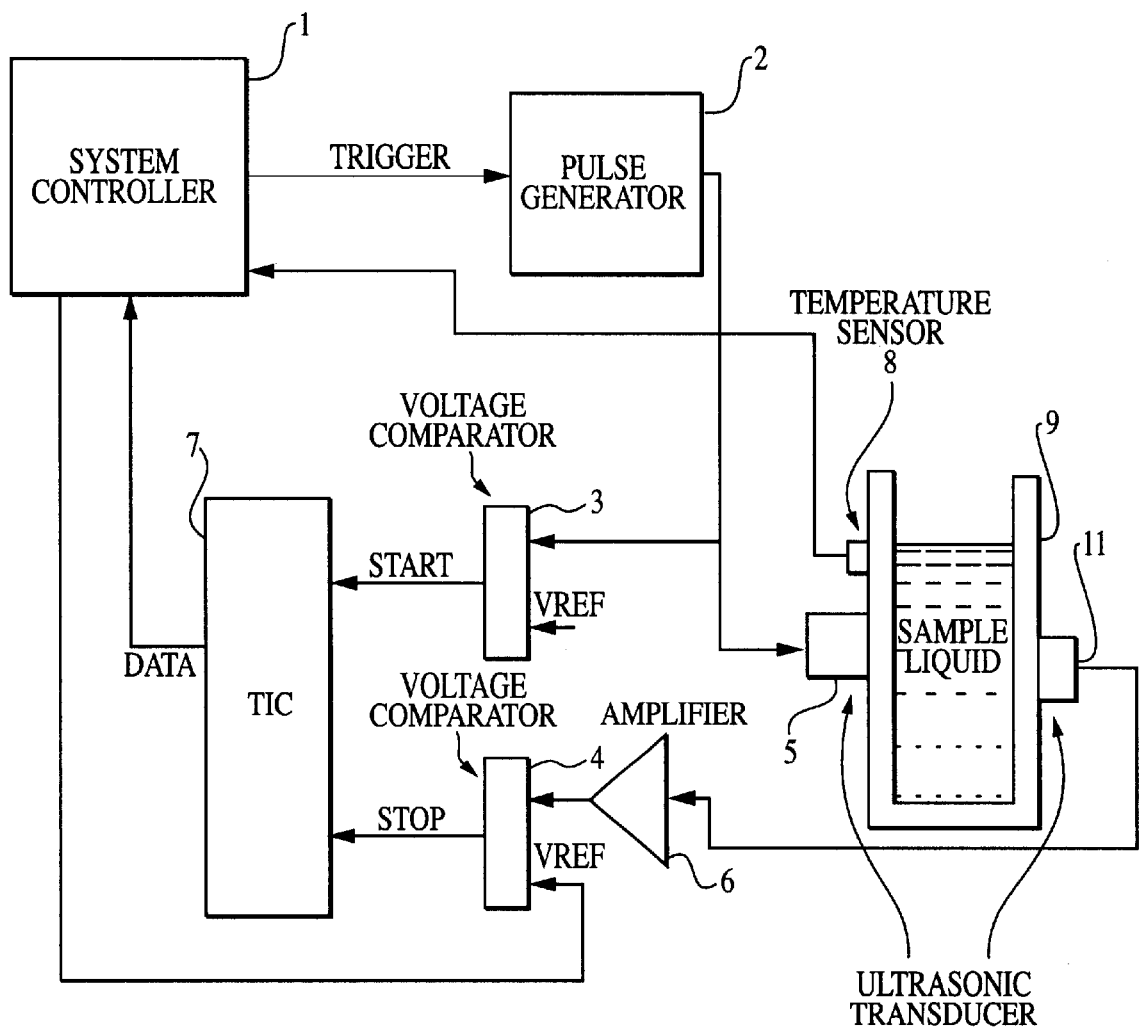
FIG. 3 is a block diagram showing the major components of another embodiment of the invention in a two-transducer system.

FIG. 3 is a schematic block diagram of an apparatus according to another embodiment of the invention. In this embodiment, a second ultrasonic transducer 11 is added to the system of FIG. 1; both transducer 5 (referred to as the "transmitting transducer" in this embodiment) and transducer 11 (referred to as the "receiving transducer" in this embodiment) are placed in operative communication with the sample vessel 9. Ultrasonic transducer 5 generates an ultrasonic wave in the sample, and ultrasonic transducer 11 detects the ultrasonic signal as it arrives at the opposite wall of the sample vessel 9, rather than allowing the signal to be reflected off the vessel 9 wall. As shown in FIG. 3, receiving transducer 11 returns the ultrasonic wave directly to voltage comparator 4 through amplifier 6. Again, amplifier 6 will not be included in the system if the signal from the ultrasonic wave after it has passed through the sample is determined to be strong enough to effect the output of voltage comparator 4 without amplification. In this embodiment, since receiving transducer 11 is not exposed to the output signal of pulse generator 2, no inhibit function is needed.

The inventive sensor system, in either embodiment, may be sized (miniaturized) as desired; the use of TIC 7 in particular allows the miniaturization of the system. The electronics (properly packaged), which, in operation, are physically separate from, but electrically connected to, transducer 5 and sample vessel 9, are approximately the size of a standard deck of playing cards and may be hand-held by the user of the sensor. The dimensions of sample vessel 9 can affect the outcome of the measurement and are primarily governed by the amount of attenuation that can be tolerated in the signal. For example, the longer the path through the sample traveled by the ultrasonic wave, the more attenuation in the signal; however, the longer the path, the more change in transit time resulting in a clearer reading of the property of interest. If the path is too long, there is greater background noise; therefore, approximately 1–1.5 inches is the longest acceptable dimension for vessel 9. One version of vessel 9 that has been fabricated is about 0.75 inch×0.75 inch×1.5 inch in size. Walls of about 0.6 inch in length have also been used. Also, since the TIC has a dynamic range of approximately 32 microseconds (with two nanoseconds of resolution and four nanoseconds of accuracy), spacing and dimensions primarily depend on the nature of the sample, e.g., if a liquid sample is unusually dense. The electronics (properly packaged) are approximately 2 inches×3 inches ×$\frac{3}{8}$ inches (or the size of a standard deck of playing cards).

There are many readily available components that can be used for the circuits shown in FIGS. 1 and 3. Except for the TIC, the major components of the sensor system (system controller, generators, transducer(s), temperature sensor, amplifier, etc.) are off-the-shelf items that are made by several manufacturers. Preferably, the transducers are high frequency to enhance the resolution of the desired fluid constituent measurement; as a practical matter, the highest possible frequency is typically used in order to obtain the best measurement resolution, e.g., 10 MHz, or even 20 MHz. The voltage comparator(s) may be a chip having one or more integrated circuits; for instance, one chip with one, two or four circuits may be used.

With regard to the timing interval counter, the TIC is a high-density, low-power electrical circuit utilizing Complimentary Metal Oxide Semiconductor (CMOS) logic technology for measuring the time interval between the occurrence of an initial electrical pulse and a subsequent electrical pulse. The TIC is capable of providing a measurement of arbitrarily long time intervals with high resolution and may be assembled with relatively low-speed, low-power, inexpensive, high-density CMOS technology. Again, it provides measurement of time intervals of up to thirty-two microseconds in duration with two nanoseconds of resolution and four nanoseconds of accuracy while utilizing an 8 MHz clock. The TIC has a dual interpolator circuit (one interpolator circuit for each pulse stretcher circuit) which performs interpolation of the time interval between the electrical pulse and the rising edge of the clock pulse which is the second clock pulse to occur after the pulse rising edge. The physical size of the TIC is minimized because the input circuit block, start counter, stop counter, arithmetic logic unit, main counter and auto-calibration block are all formed on a single forty-four (44) pin grid array completely using CMOS technology, such as the UT160D chip manufactured by United Technologies. CMOS technology is employed in the pulse stretcher and other respective circuits to minimize power consumption. Also, both pulse stretchers are implemented on a single twenty-six (26) lead flat-pack hybrid microcircuit. The total operating power for both the UT160D chip and the hybrid is limited to two hundred (200) milliwatts.

Rather than using a high-speed, typically high-power, voltage comparator, the interpolator circuit incorporates a simple CMOS inverter and an analog switch as a comparator by implementing an autobalance technique, which significantly lowers power consumption of the circuit without affecting accuracy. Both critical matching transistor characteristics and temperature compensation of the interpolator circuit are not required because of the auto-calibration feature of the TIC implemented within the gate array. The TIC has been further described in U.S. Pat. No. 5,333,162, incorporated herein by reference.

In operation, according to FIG. 1, system controller 1 provides a trigger signal to pulse generator 2 to initiate a stimulus signal from pulse generator 2 to ultrasonic transducer 5. Simultaneously, system controller 1 provides an inhibit signal to voltage comparator 4 to prevent its operation during the time the stimulus signal from pulse generator 2 to ultrasonic transducer 5 is active. Voltage comparator 3 has been pre-programmed with a set (unvarying) reference voltage. The signal from pulse generator 2 causes voltage comparator 3 to switch state when the stimulus signal voltage exceeds the reference voltage, thus providing the start signal to TIC 7 and initiating the transit time measurement. Ultrasonic transducer 5 responds to the stimulus signal from pulse generator 2 by producing an ultrasonic wave and transmitting it into the sample. The ultrasonic wave passes through the sample, is reflected by the vessel 9 wall opposite the direction the signal is traveling, travels back through the sample, and imposes an echo signal on ultrasonic transducer 5. The echo signal is amplified by the amplifier 6 circuit (in cases where amplifier 6 is needed) and applied to voltage comparator 4. The duration of the inhibit signal from system controller 1 (previously described) to voltage comparator 4 is from the generation of the stimulus signal until the ultrasonic wave has returned through the sample. The inhibit signal is active until the emission of the echo signal from the sample and its passage through transducer 5 on its way to amplifier 6 (if an amplifier is included) and voltage comparator 4. The inhibit signal acts to allow the stimulus signal to settle and the transducer fibrillation to dampen.

The reference voltage for voltage comparator 4 is set (governed) by system controller 1, typically to one half of the echo signal's peak amplitude. Therefore, this reference voltage may change each time the measurement is taken depending on the peak amplitude of each echo signal, i.e., one half the peak value is recalculated by system controller 1 every time the measurement is made. The chosen algorithm for determination of this reference voltage is governed by the need to activate the stop signal and may be any value of the peak amplitude (e.g., one third or three fourths) that will cause that activation. However, accuracy problems may result if the voltage reference is chosen to be too close to, or too far from, the peak value of the echo signal. In response to receipt of an echo signal higher in value that the reference voltage for comparator 4, the circuit output of amplifier 6 causes voltage comparator 4 to switch state, providing the stop signal to the TIC 7 circuit. This completes the transit time measurement.

The TIC 7 circuit precisely measures the time elapsed between the transmitted ultrasonic wave and the echo signal. System controller 1 then reads this time interval. System controller 1 also monitors the voltage output from temperature sensor 8, thereby obtaining a measurement of the fluid sample temperature. Transit time and temperature data are compared to calibration data stored the memory of system controller 1, and the sample property of interest is then computed. System controller 1 outputs this property value in any of several known methods. If desired, these steps may be repeated several times, and averaging techniques are applied to attain a more accurate value for the desired property of interest.

The operation of FIGS. 1 and 3 is quite similar. Either embodiment (that of FIG. 1 or FIG. 3) processes the electrical signals produced in response to ultrasonic waves transmitted by transducer 5 and detected by either transmitting transducer 5 itself (as in FIG. 1) or by receiving transducer 11 (as in FIG. 3). In the single transducer system of FIG. 1, the single ultrasonic transmitter/receiver transducer 5 is connected to both pulse generator 2 and echo signal amplifier 6. In the two-transducer system of FIG. 3, transmitting transducer 5 is connected to pulse generator 2, and receiving transducer 11 is connected to echo signal amplifier 6. Pulse generator 2, in either embodiment, energizes transmitting transducer 5 to produce high frequency (e.g., 3–20 MHz), short duration (e.g., 1–10 microseconds), pulsed ultrasonic waves. The parameters desired for the waves are not customized specifically for this application and are essentially the same in both embodiments. The choice of transducer is driven by the need for a wave with the highest possible frequency that will give the best possible attenuation, although, in the two-transducer embodiment, a wave with as much power may not be needed.

The ultrasonic waves produced by transducer 5 serially pass through transducer 5, the sample, receiving transducer 11, and amplifier 6. System controller 1 controls the rate of pulse produced by pulse generator 2. The pulse amplitude is typically 5 to 20 volts, preferably with a rise-time of less than 20 nanoseconds. It should be noted that the sensor system of the invention requires much lower voltage than required for other sensors. Other than that reflection of the echo signal is accomplished by receiving transducer 11 in FIG. 3, rather than by the wall of vessel 9 as in FIG. 1, and the elimination of the inhibit function of FIG. 1, operation using the FIG. 3 system is identical to that described above for the apparatus of FIG. 1.

Figure 4A:
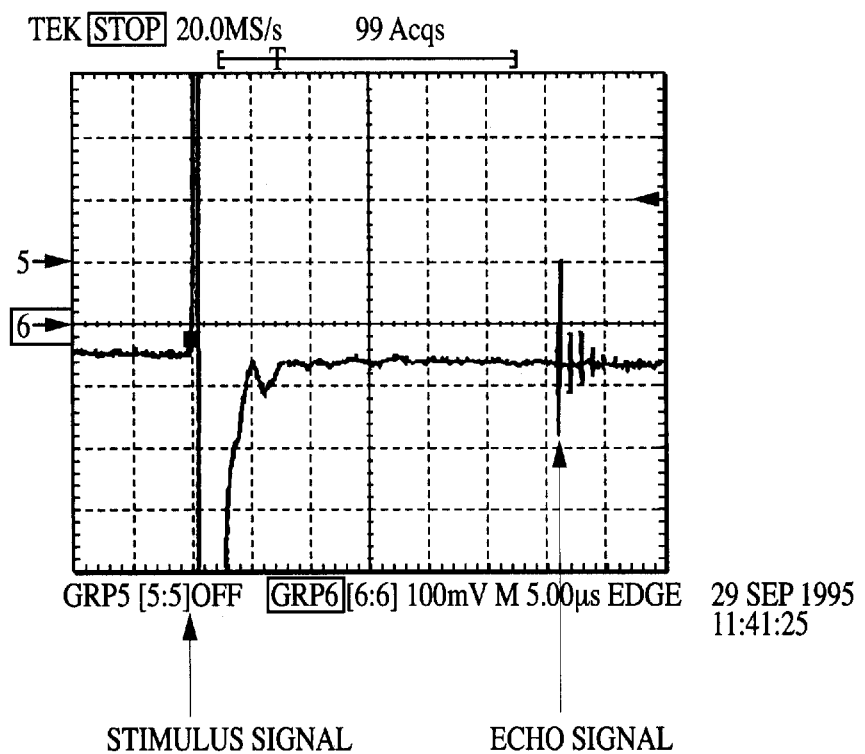
FIG. 4A is a graph of the complete stimulus/echo signal waveform at the transducer and amplifier output.
Figure 4B:
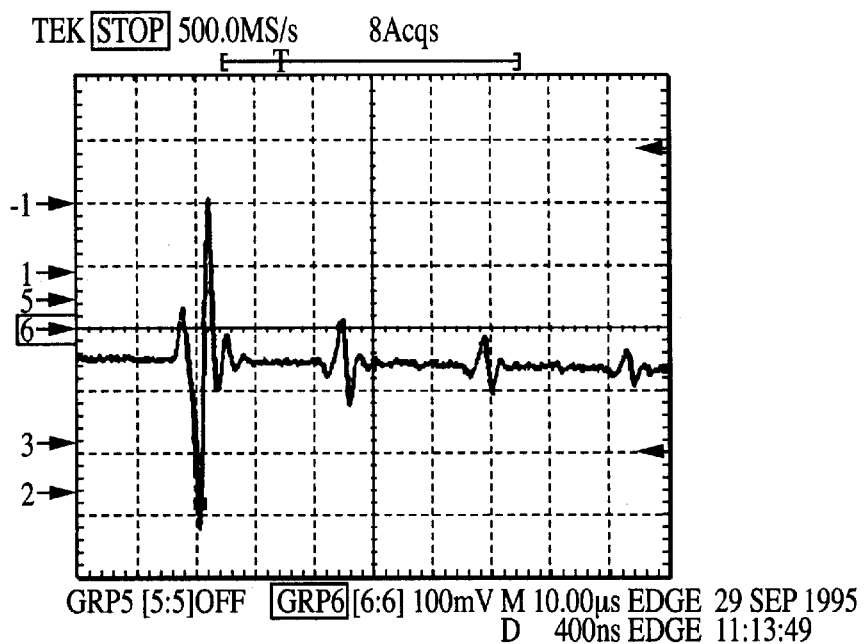
FIG. 4B is an expanded view of the echo signal waveform from FIG. 4A.

The analog portions of the sensor system have been built and tested, with satisfactory results. Typical waveforms are shown in FIGS. 4A and 4B. FIG. 4A is a graph of the complete stimulus/echo signal waveform detected over time using a single planar transducer, such as transducer 5, the waveform being taken at the output of amplifier 6. For this test, the structural configuration was that of FIG. 1, with transducer 5 mounted on vessel 9 and a planar sensor element with a planar protective facing material (not shown) included. (The ultrasonic transducer 5 stimulus signal pulse of FIG. 1 is the stimulus signal of FIG. 4A.) The waveform is one wave traveling directly through the liquid sample. FIG. 4B is an expanded view of the echo signal waveform shown in FIG. 4A.

As shown in FIG. 4A, the stimulus pulse from pulse generator 2 causes the signal to go off scale. However, amplifier 6 recovers quickly enough to sense the echo signal, which occurs approximately 32 microseconds after the stimulus pulse from transducer 5. Timing measurements are made between the rising edge of the stimulus signal to transducer 5 and the rising edge of the return echo signal received by transducer 5. It is important to note that the exact point chosen on the echo signal for the time interval measurement (such as 50% of peak amplitude) is somewhat arbitrary, but whatever is chosen, consistency should be maintained to improve measurement accuracy.

The accuracy of the inventive sensor system depends both on the ability to accurately measure temperature variations and the accuracy of the TIC 7 circuit. In water, as an example, transit time variation with temperature is on the order of 0.25% per degree Centigrade. For velocity measurement errors to be kept under 10 parts per million (ppm), temperature variations of 0.004° C. must be detectable. Also, the TIC 7 circuit must have an accuracy of better than 10 ppm to keep velocity measurement errors under 10 ppm.

To obtain temperature data, the temperature of the liquid sample is measured, and the measurements are used to correct the calculation of the liquid sample composition for temperature changes. For liquid samples with slowly varying temperatures, temperature sensor 8 is mounted on the external wall of vessel 9 (because vessel 9 and the liquid being tested are expected to be at approximately the same temperature). In this case, the sensor housing is covered with insulation to minimize the effect of temperature changes in the environment. For rapid temperature changes in a liquid sample, temperature sensor 8 is inserted directly into the liquid sample, as is temperature sensor 8 in the FIG. 3 view. Multiple readings enhance measurement accuracy. For temperature variations, the data obtained by the sensor system of the present invention provide a family of curves, from which the property(ies) of interest can be derived. Also, it should be noted that, since the transit time of a liquid is dependent on, or sensitive to, temperature, the inventive sensor system can be used to accurately measure temperature of a known liquid.

The inventive sensor system has numerous applications. A general application is remote monitoring of liquids for real-time reporting of state. More specifically, in automobiles, the deterioration of a liquid-like engine oil or transmission fluid can be measured. In industrial process control, liquid level in a container, the amount of an additive in a liquid, or any specific characteristic of interest of a liquid can be monitored. In the food industry, deterioration of cooking oils or other liquids can be monitored. In the field of medicine, specific properties of bodily fluids can be monitored. The inventive sensor may also be used in the detection of impurities in groundwater which, like salt in seawater, cause a change in velocity of the ultrasonic wave and thus a change in transit time of that wave through a groundwater sample.

Advantageously, the present invention provides a sensor system capable of autonomous remote operation, which can be remotely queried and which can provide a response tailored to predetermined queries, without hands-on constant adjustment of the sensor and without requiring the presence of the system operator, i.e., with virtually no need for manual adjustment during normal operation. In addition, the sensor system of the present invention is capable of operation in-situ and with initial calibration only. Further, the inventive sensor is capable of operation within environments exhibiting extreme ranges of temperature, pressure, and pH. Yet another advantage is that the sensor system of the present invention can be inserted into very small spaces and is easily integrated into existing process control systems.

Although the invention has been described in detail with particular reference to these preferred embodiments, other embodiments can achieve the same results. Variations and modifications of the present invention will be obvious to those skilled in the art, and it is intended to cover in the appended claims all such modifications and equivalents.

What is claimed is:

1. A sensor system for measuring the transit time of an ultrasonic wave through a liquid sample, comprising:

(a) a vessel of known dimensions for containing said liquid sample;

(b) an ultrasonic means, having an ultrasonic transducer means operably connected to said vessel in communication with said liquid sample and having an electric pulse generator operably connected to said transducer means, for generating and sending an ultrasonic wave through said liquid sample upon receipt of a trigger pulse;

(c) a system controller means having a trigger signal output for generating said trigger pulse;

(d) a high-resolution, low-power, time interval counter, having a start input gating means and a stop input gating means each operably connected to said controller means and said transducer means;

(e) said start gating means and said stop gating means consisting of at least two voltage comparator means comprising a first voltage comparator means, said first comparator means being preprogrammed with an unvarying first reference voltage of a chosen value, for receiving an electrical pulse signal from said generator, for comparing the voltage of said electrical pulse signal to said first reference voltage, and for providing a start signal to said counter when the voltage of said electrical pulse signal exceeds said first reference voltage, and a second voltage comparator means for receiving a second variable reference voltage from said controller means, said second reference voltage being set by said controller means to a predetermined percentage of a peak amplitude of an echo pulse, said echo pulse derived from said ultrasonic wave after said ultrasonic wave has passed through said liquid sample, for comparing the voltage of said echo pulse to said second reference voltage, and for providing a stop signal to said counter when the voltage of said echo pulse exceeds said second reference voltage; and (f) a time interval data readout means for providing a time interval between said start signal and said stop signal; wherein said trigger pulse from said controller means causes said pulse generator to provide said electric pulse signal simultaneously to said start gating means and to said transducer means, which causes said transducer means to produce said ultrasonic wave, said ultrasonic wave being sent through said liquid sample and from said liquid sample to said stop gating means, which causes said stop gating means to produce said stop signal to said counter, and wherein said data readout means provides time measurements between said start signal and said stop signal to said controller means.

2. The sensor system of claim 1, further comprising an amplifying means, operably connected to said stop gating means and inserted between said transducer means and said stop gating means, for amplifying said ultrasonic wave provided by said transducer means after said ultrasonic wave has passed through said liquid sample and for sending an amplified ultrasonic wave to said stop gating means.

3. The sensor system of claim 1, wherein said controller further comprising a means for providing an inhibit signal to said stop gating means simultaneously when providing said trigger signal to said generator, to prevent operation of said stop gating means while said electronic pulse signal is being transmitted and while said ultrasonic wave is being transmitted through said liquid sample.

4. The sensor system of claim 1, wherein said second reference voltage is set to one-half of said peak amplitude of said echo pulse.

5. The sensor system of claim 1, further comprising a means for measuring temperature variations in said liquid sample and a means for providing data representing said temperature variations to said controller means, wherein said time measurements provided to said controller means are mathematically corrected by said data representing said temperature variations.

6. The sensor system of claim 1, wherein said controller means further comprises:

a means for storing at least one predetermined reference transit time for a reference sample, said reference transit time being chosen from a plot of a selected characteristic of the reference sample versus a plurality of transit times;

a means for comparing transit time measurements received from said counter to the reference transit time;

a means for calculating the actual value of a selected characteristic in the sample using the comparison of the transit time measurements to the reference transit time; and a means for displaying the value of the selected characteristic to a user of the sensor system.

7. The sensor system of claim 1, for identifying the presence of non-conforming constituents in said liquid sample.

8. The sensor system of claim 1, wherein said transducer means is a high-frequency ultrasonic transducer having a frequency range of 10–20 MHz.

9. The sensor system of claim 1, wherein said transducer means is a piezoelectric ultrasonic transducer.

* * * * *